United States Patent
Hanada et al.

(12)

(10) Patent No.: US 6,280,754 B1
(45) Date of Patent: Aug. 28, 2001

(54) DERMAL TOPICAL FORMULATIONS

(75) Inventors: Minoru Hanada; Eiko Tamai; Kazuhiko Tokoro, all of Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/432,100

(22) Filed: Nov. 2, 1999

(30) Foreign Application Priority Data

Nov. 2, 1998 (JP) .................................................. 10-312047

(51) Int. Cl.[7] ............................. A61K 9/00; A61K 7/135
(52) U.S. Cl. ............................ 424/401; 424/62; 514/946; 514/947
(58) Field of Search ................................ 424/401, 61, 62, 424/59, 60, 78.02, 400, 403

(56) References Cited

U.S. PATENT DOCUMENTS

| 5,545,399 | * | 8/1996 | Lee et al. ............................... 424/59 |
| 5,716,602 | * | 2/1998 | Uick ....................................... 424/59 |
| 5,989,527 | * | 11/1999 | Siegfried et al. ...................... 424/59 |

* cited by examiner

*Primary Examiner*—Thurman K. Page
*Assistant Examiner*—Blessing Fubara
(74) *Attorney, Agent, or Firm*—Kubovcik & Kubovcik

(57) ABSTRACT

A dermal topical formulation containing p-menthane-3,8-diol and a whitening component such as arbutin, kojic acid, ellagic acid, ascorbic acid or its derivative, lactic acid, glycolic acid, tartaric acid, and an essence or an absolute extracted from a plant such as labdanum, jasmine and mugwort (T.vulgare). The dermal topical formulation is highly safe and capable of promoting the percutaneous absorption of the whitening component.

4 Claims, No Drawings

DERMAL TOPICAL FORMULATIONS

FIELD OF THE INVENTION

The present invention relates to a dermal topical formulation containing a whitening component and a percutaneous absorption promoting agent and, more particularly, to a dermal topical formulation containing a whitening component and p-menthane-3,8-diol.

BACKGROUND OF THE INVENTION

Whitening cosmetics which contain a substance having a whitening effect as an active ingredient for preventing dermal pigmentation or formation of spots or freckles due to the sunburn have been proposed. For example, a whitening cosmetic containing a placenta extract or a vitamin C derivative as an active ingredient with or without a vegetable extract or an α-hydroxylic acid (lactic acid, glycolic acid, etc) as a moisturizing component for enhancing the expected efficacy of such an active ingredient has been proposed.

On the other hand, based on findings that tyrosinase is involved in a melanin biosynthesis mechanism which is associated with dermal pigmentation, a whitening skin care product containing, as an active ingredient, arbutin or kojic acid which has a tyrosinase activity inhibiting effect has also been proposed.

However, the biosynthesis of melanin is known to take place in a melanocyte present in the basal layer which is the deepest place in an epidermis. It is also known that a corneal layer which forms a surface of human skin has a physiological function as a barrier against the invasion of to foreign bodies from an extracorpreal region. Therefore, application to the skin of a simple mixture of a whitening component with a commonly used cosmetic formulation base allows only a trace amount to penetrate the corneal layer to reach the basal layer and makes it difficult for the efficacy of the whitening component to be exerted. Accordingly, various percutaneous absorption promoters have been proposed and employed in the fields of pharmaceuticals and cosmetics for the purpose of facilitating the absorption of an active ingredient via the skin.

Nevertheless, problems still exist which include the difficulty in selecting an optimum combination of a whitening component and a known percutaneous absorption promoter as well as the absence of satisfactory efficacy and safety which should be possessed by a dermal topical formulation. In addition, increasing the whitening component content in a formulation in an attempt to increase the whitening effect based on the fact that the whitening component can itself be slightly absorbed via the skin is not recommended since it is problematic in terms of safety and cost.

OBJECT OF THE INVENTION

An object of the present invention is to provide a dermal topical formulation which exhibits an excellent percutaneous absorption of a whitening component, has a high whitening effect and is highly safe.

DETAILED DESCRIPTION OF THE INVENTION

In commonly owned U.S. patent application Ser. No. 09/388,482 it is disclosed that p-menthane-3,8-diol, which is derived from an eucalyptus plant and has a mosquito repelling effect, has a dermal absorption-promoting effect and can be used as a cosmetic formulation base because of its high safety. We conducted further research and found that the percutaneous absorption of a whitening component can be promoted by combining this compound with the whitening component, whereby the present invention was established.

Thus, the present invention provides a dermal topical formulation comprising a whitening component and p-menthane-3,8-diol.

p-Menthane-3,8-diol employed in the present invention is a colorless, odorless and viscous substance, and exists as any of 4 isomers, namely, (+)-cis-p-menthane-3,8-diol, (−)-cis-p-menthane-3,8-diol, (+)-trans-p-menthane-3,8-diol and (−)-trans-p-menthane-3,8-diol. The substance usually exists as a mixture of a cis form and a trans form, and may be used in the invention as a mixture, for example, as a mixture having a cis:trans ratio of 6:4, but any of the isomers listed above can appropriately be selected for use.

p-Menthane-3,8-diol has no skin irritating effect, and is highly safe, and promotes the percutaneous absorption of a whitening component when combined with such a whitening component.

A whitening component employed in combination with p-menthane-3,8-diol in the invention may, for example, be arbutin, kojic acid, ellagic acid, ascorbic acid, an ascorbic acid derivative, and an α-hydroxylic acid such as lactic acid, glycolic acid and tartaric acid. Further examples are whitening components contained in an essence or an absolute extracted from a plant such as labdanum (Cistus ladaniferus L., Cistaceae), jasmine (Jasminum officinale L., Oleaceae) and mugwort (Tanacetum vulgare L., Compositae) which are especially known, among plant-derived essences or absolutes, to have whitening activities.

In a dermal topical formulation according to the invention, a whitening component and p-menthane-3,8-diol can be contained in a weight ratio of 5:95 to 95:5. p-menthane-3,8-diol can be incorporated into the formulation base in an amount which will vary depending on the intended uses and the formulation characteristics, and which is within a range of 0.01 to 20% by weight, preferably 0.1 to 10% by weight, based on the entire amount of the dermal topical formulation. An amount of less than 0.01% by weight results in an insufficient percutaneous absorption-promoting effect, while an amount exceeding 20% by weight results in poor formulation stability.

In addition to a whitening component and p-menthane-3,8-diol as a percutaneous absorption promoter, components usually incorporated into pharmaceuticals and cosmetics as a formulation base can also be contained in the dermal topical formulation according to the invention. Such components include for example, fats, waxes, surfactants, humectants, antioxidants, organic acids, alkalis, pigments, dyes, fungicidal preservatives, resins, pH modifiers, UV absorbers, chelating agents, thickening agents, alcohols, water, fragrances and the like.

A dermal topical formulation containing a whitening component and p-menthane-3,8-diol according to the invention may be prepared in an application form which is appropriately selected based on the purpose and mode of use, and includes ointments, creams, sprays, lotions, gels, sols, aerosols, plasters, tapes and the like.

As long as the object of the present invention is achieved, a formulation base and a carrier used to formulate the dermal topical formulation can be appropriately selected and employed based on the intended use, the formulation characteristics and the mode of use of the dermal topical formulation.

A dermal topical formulation containing a whitening component and p-menthane-3,8-diol according to the invention increases the percutaneous absorption efficiency of the whitening component and is highly safe. Since the percutaneous absorption of a whitening component is efficiently promoted, a reduced amount of the whitening component can be employed and a moisturizing effect can also be expected.

EXAMPLES

The present invention is described in further detail in the following examples, which examples are not intended to limit the scope of the invention.

Example 1

Each of arbutin (Nacalai tesque, Inc.) and kojic acid (Nacalai tesque, Inc.) was combined with p-menthane-3,8-diol (MDM) to examine the penetration of the substances through the skin.

MDM employed was a mixture of the trans form and the cis form (cis:trans=6:4).

(1) Sample Formulation

According to the formulations shown below, each of arbutin and kojic acid was combined with MDM, dissolved in ethanol and admixed with water to prepare a sample. The samples thus prepared were kept at 37° C. until use.

As a control, arbutin or kojic acid which was not combined with MDM was employed.

TABLE 1

Arbutrin sample formulation

|  |  | Invention | Control |
|---|---|---|---|
| Water | (ml) | 6.0 | 6.0 |
| Ethanol | (ml) | 4.0 | 4.0 |
| Arbutrin | (mg) | 100.0 | 100.0 |
| MDM | (mg) | 300.0 | 0 |

TABLE 2

Kojic acid sample formulation

|  |  | Invention | Control |
|---|---|---|---|
| Water | (ml) | 6.0 | 6.0 |
| Ethanol | (ml) | 4.0 | 4.0 |
| Kojic acid | (mg) | 100.0 | 100.0 |
| MDM | (mg) | 300.0 | 0 |

(2) Dermal Penetration Test

The test was performed in accordance with a method by Fujii et al (Biol. Pharm. Bull., 20 (3), 249, 1997 and Drug Delivery System 12(2), 127, 1997). Thus, a skin of a Yucatan Micropig (5 month old female, Nippon Charles River) stored frozen at −80° C. was thawed at room temperature for 30 minutes, made free from excessive subcutaneous fat layer and then cut into pieces of about 2 cm square, which were subjected to the penetration test.

In the penetration test, a modified Franz type diffusion cell (valid surface area: 1.1 $cm^2$, receptor phase 16 ml, IWASHIYA) filled with a phosphate buffer, pH 7.1, was employed as a receptor phase chamber, which was stirred with a magnetic stirrer and kept at 37° C. 0.5 ml of a sample solution was added to a donor chamber, which was covered with glass beads to avoid the evaporation of the sample solution. Upon each sampling at a certain interval, the same volume of the buffer solution was supplemented. A receptor phase thus fractionated was subjected to high pressure liquid chromatography (HPLC) to quantify the analyte which had penetrated. The penetration test was conducted over a period as long as 30 hours.

(3) HPLC Operating Conditions
  Instrument: LC module 1 (NIPPON WATERS)
  Column: TSK-GEL ODS120T 4.6 mm×150 mm (TOSOH)
  Mobile phase: For arbutin, Methanol:0.1% phosphoric acid=3:97; For kojic acid, Methanol:0.1% phosphoric acid= 5:95
  Flow rate: 1 ml/min (4) Detection of Analytes
  Waters 486 tunable UV/visible absorbance detector was employed to determine arbutin at 285 nm and kojic acid at 270 nm.

(5) Data Processing
  ChromatoPak CR-3A (Shimadzu) was used to determine a peak area of each analyte, from which a calibration curve was obtained separately and a concentration was calculated.

(6) Evaluation of Percutaneous Absorption Promoting Effect

The percutaneous absorption promoting effect of p-menthane-3,8-diol was evaluated by measuring the amount per 1 $cm^2$ of cumulative penetration into the receptor phase of the YMP skin after a certain time period compared to that of a control as shown in the following equation.

The absorption promoting effect=Cumulative amount of analyte penetrated from sample/Cumulative amount of analyte penetrated from control The results are shown in Table 3.

TABLE 3

Percutaneous absorption promoting effect

| Elapsed time | 24 hours | 30 hours |
|---|---|---|
| Control | 1.0 | 1.0 |
| Arbutrin | 2.5 | 1.7 |
| Kojic acid | 4.1 | 2.7 |

As evident from Table 3, both of arbutin and kojic acid exhibited higher penetrations in the presence of p-menthane-3,8-diol as compared to the respective controls.

Example 2

UV-induced Pigmentation Reducing Effect in Guinea Pigs

The dorsal area of each of 5 brown guinea pigs per group was clipped carefully and the clipped area was covered with a shield having 2 openings, each opening being 2.5×2.5 cm. The area was irradiated with a UV light in UVB range at an intensity of 300 $mj/cm^2$ once a day for three consecutive days. Immediately after the UV irradiation, application was begun to the irradiation site of a 50 $\mu l$ aliquot of a sample dissolved in ethanol. Application was continued for 28 days, twice a day in the morning and in the evening, whereby a reduction in the pigmentation spots was effected, which was examined on the dates indicated in Table 4.

The test animals were three groups of guinea pigs, in the first of which the left side of the median line of a guinea pig was treated only with a 5% by weight solution of kojic acid while the right side was treated with a 5% by weight solution of kojic acid supplemented with 0.5% by weight of p-menthane-3,8-diol (MDM). In the second group, the left side was treated only with a 3% by weight solution of kojic acid in a similar manner, while the right side was treated with a 3% by weight solution of kojic acid supplemented with 0.5% by weight of p-menthane-3,8-diol. In the third group, the left side was treated with a 0.5% by weight solution of p-menthane-3,8-diol, while the right side was treated with ethanol only as a control.

Activity was evaluated by measuring L value of each application site with a calorimeter (MINOLTA CAMERA, CR2006) followed by subtracting from an initial value $L_o$ observed at the application site immediately before application of a sample a value $L_x$ (later value) observed after application of a sample. The resultant value was $\Delta L$.

A smaller value of $\Delta L$ obtained by the following equation represents a whiter skin.

$\Delta L = L_0 - L_x$ $L_0$: Value L of target site (sample application site) before application of sample $L_x$: Value L of target site (sample application site) 7, 14, 21 or 28 days after application of a sample The results are shown in Table 4.

TABLE 4

Change in value ($\Delta L$)

| Sample Composition | | value $\Delta L$ After | | | |
|---|---|---|---|---|---|
| No. | Kojic acid | MDM | 7 days | 14 days | 21 days | 28 days |
| 1 | 5.0% | 0.5% | 2.97 | 5.00 | 4.59 | 4.56 |
| 2 | 5.0% | — | 3.60 | 5.42 | 5.74 | 5.78 |
| 3 | 3.0% | 0.5% | 3.78 | 5.06 | 4.02 | 3.84 |
| 4 | 3.0% | — | 4.30 | 6.26 | 5.55 | 5.09 |
| 5 | — | 0.5% | 3.34 | 5.16 | 4.40 | 3.96 |
| 6 | — | — | 2.78 | 4.66 | 4.24 | 3.55 |

As evident from Table 4, a comparison of the data of sample No.1 with No.2 and of sample No.3 with No.4, corresponding to 5% and 3% by weight of kojic acid, respectively, each given with and without 0.5% by weight of p-menthane-3,8-diol, revealed that the application of a mixture of kojic acid and p-menthane-3,8-diol resulted in a lower value of $\Delta L$ than application of kojic acid alone, and exhibited a markedly higher pigmentation reducing effect.

A comparison of the data of Samples No.5 and 6, which corresponded to treatments with 0.5% by weight of p-menthane-3,8-diol alone and with ethanol alone, respectively, revealed no pigmentation reducing effect of p-menthane-3,8-diol by itself.

A difference in $\Delta L$ is attributable to the difference between groups.

What is claimed is:

1. A dermal topical formulation consisting essentially of a whitening component and p-menthane-3,8-diol.

2. A dermal topical formulation according to claim 1 wherein said whitening component is selected from arbutin and kojic acid.

3. A dermal topical formulation according to claim 1 wherein the weight ratio of said whitening component to p-menthane-3,8-diol is 5:95 to 95:5.

4. A dermal topical formulation according to claim 1 wherein p-menthane-3,8-diol is contained in an amount of 0.01 to 20% by weight.

* * * * *